United States Patent
Pascolo

(10) Patent No.: US 9,636,414 B2
(45) Date of Patent: May 2, 2017

(54) PARTICLES COMPRISING SINGLE STRANDED RNA AND DOUBLE STRANDED RNA FOR IMMUNOMODULATION

(75) Inventor: Steve Pascolo, Zurich (CH)

(73) Assignee: BIONTECH AG, Mainz (DE)

( * ) Notice: Subject to any disclaimer, the term of this patent is extended or adjusted under 35 U.S.C. 154(b) by 0 days.

(21) Appl. No.: 14/361,827

(22) PCT Filed: Dec. 15, 2011

(86) PCT No.: PCT/EP2011/006358
§ 371 (c)(1),
(2), (4) Date: Jul. 8, 2014

(87) PCT Pub. No.: WO2013/087083
PCT Pub. Date: Jun. 20, 2013

(65) Prior Publication Data
US 2014/0348924 A1    Nov. 27, 2014

(51) Int. Cl.
| | | |
|---|---|---|
| *A61K 48/00* | (2006.01) |
| *C12N 15/11* | (2006.01) |
| *C07H 21/02* | (2006.01) |
| *C07H 21/04* | (2006.01) |
| *A61K 47/48* | (2006.01) |
| *A61K 9/16* | (2006.01) |
| *A61K 31/7105* | (2006.01) |
| *A61K 31/713* | (2006.01) |
| *A61K 39/385* | (2006.01) |
| *A61K 39/00* | (2006.01) |

(52) U.S. Cl.
CPC ........ *A61K 47/4833* (2013.01); *A61K 9/1658* (2013.01); *A61K 31/713* (2013.01); *A61K 31/7105* (2013.01); *A61K 39/385* (2013.01); *A61K 2039/58* (2013.01); *A61K 2039/62* (2013.01)

(58) Field of Classification Search
USPC ........................... 536/23.1, 24.3, 24.33, 24.5
See application file for complete search history.

(56) References Cited

U.S. PATENT DOCUMENTS

| | | |
|---|---|---|
| 2003/0232074 A1 | 12/2003 | Lipford et al. |
| 2007/0142315 A1 | 6/2007 | Forsbach et al. |
| 2010/0297176 A1 | 11/2010 | Haixiang |

FOREIGN PATENT DOCUMENTS

WO    2009/144230    12/2009

OTHER PUBLICATIONS

Clusel et al. (Nucleic Acids Research, 1993 vol. 21, No. 15:3405-3411).*
Park et al. (BBRC, 2000 vol. 270:953-960).*
Billiau et al. (Proc Soc Exp Biol Med. Nov. 1969;132(2):790-6).*
(Continued)

*Primary Examiner* — Terra C Gibbs
(74) *Attorney, Agent, or Firm* — McAndrews, Held & Malloy, Ltd.

(57) ABSTRACT

The present invention relates to chimeric particles comprising single stranded RNA (ssRNA), double stranded RNA (dsRNA) and at least one cationic agent, a pharmaceutical composition containing said particles and to a method of producing the same. The particles of the present invention are particularly useful as an immunostimulating medicament with a superlative pattern of immunostimulation.

23 Claims, 6 Drawing Sheets

(56) References Cited

OTHER PUBLICATIONS

Chandra et al. (Z. Krebsforsch, 1971 vol. 74:40-44).*
Steinberg et al. (Medical Sciences, 1969 Vo. 163:1102-1107).*
Pitha et al. (J. Gen. Virol. 1972 vol. 15:89-92).*
Int'l Preliminary Report for Int'l Patent Application No. PCT/EP2011/006358, mailed Jun. 17, 2014.
Hornung V. et al., 2002, J. Immunol. 168, 4531-4537.
Jarrossay D. et al., 2001, Eur. J. Immunol. 31, 3388-3393.
Sandor F. and Buc, M., 2005, Folia Biologica (Praha) 51, 188-197.
Rettig L. et al., 2010, Blood 115,4533-4541.
Leuenberger, et al. (1995) Helvetica Chimica Acta, CH-4010 Basel, Switzerland.
Sambrook, et al. Molecular Cloning: A Laboratory Manual, 2nd Edition, Cold Spring Harbor Laboratory Press, Cold Spring Harbor 1989.
International Search Report for International Patent Application No. PCT/EP2011/006358, mailed Jul. 13, 2012.

* cited by examiner

SEQUENCE LISTING

<160> NUMBER OF SEQ ID NOS: 1

<210> SEQ ID NO 1
<211> LENGTH: 18
<212> TYPE: RNA
<213> ORGANISM: Artificial Sequence
<220> FEATURE:
<223> OTHER INFORMATION: Oligonucleotide

<400> SEQUENCE: 1
aguguuauuc uuguaugg                                                 18

PARTICLES COMPRISING SINGLE STRANDED RNA AND DOUBLE STRANDED RNA FOR IMMUNOMODULATION

The present invention relates to immunomodulating particles comprising single stranded RNA and double stranded RNA, a pharmaceutical composition comprising said particles and to a method of producing the same. The particles of the present invention are particularly useful as immunomodulating medicament with superlative and unexpected biological activities.

BACKGROUND OF THE INVENTION

The immune system senses infections (e.g. virus or bacteria) as well as pathologic situations (e.g. necrosis) by the detection of danger signals termed respectively PAMPs (Pathogens-Associated Molecular patterns) and DAMPs (Damage Associated Molecular Patterns). Those molecular signals are detected by several families of specific receptors termed pattern recognition receptors (PRRs). PAMPS can be proteins (e.g. flagellin from bacteria), conjugated lipids such as lipopolysaccharides (LPS), or nucleic acids. In this later family, different forms of mislocalized nucleic acids are recognized by different PRRs present in endosomes: unmethylated CpG motifs in bacterial DNA are detected by Toll Like Receptor (TLR)-9, single stranded RNA (ssRNA) is detected by TLR-7 and TLR-8 while double stranded RNA (dsRNA) is detected by TLR-3. Those receptors are expressed in distinct cell populations (Hornung V. et al., 2002, J. Immunol. 168, 4531-4537 and Jarrossay D. et al., 2001, Eur. J. Immunol. 31, 3388-3393) and trigger different intracellular signals that result in different types of immunostimulation i.e. induction of different types of cell surface activation markers and of different types of cytokines. For example, stimulation through TLR-7 is particularly efficacious to trigger interferon-alpha production while stimulation through TLR-3 is particularly efficacious to trigger interferon-beta production (Sandor F. and Buc, M., 2005, Folia Biologica (Praha) 51, 188-197). Of interest, pathogens and pathological situations can trigger more than one PRR. For example Gram-negative bacteria can stimulate innate immunity through TLR-4 by LPS and also through TLR-9 by DNA. Thereby, several cell types get activated and consequently cumulative immune responses can be triggered. This fact was overlooked and synthetic PAMP formulations developed with the goal of inducing therapeutic immunomodulation to fight chronic diseases such as persistent virus infections or cancer use one single PAMP. Using ssRNA it was recently reported that a clinically acceptable immunostimulating formulation can be obtained by combining in specific conditions (i.e. low salts) the natural cationic peptides termed protamine and ssRNA (Rettig L. et al., 2010, Blood 115, 4533-4541 and WO 2009/144230). This formulation activates TLR-7 and TLR-8 but as expected not TLR-3.

The present invention is based on the observation that in adequate conditions ssRNA and dsRNA can be co-formulated into particles. The immunostimulation obtained by these ssRNA/dsRNA particles is unexpectedly higher than the immunostimulation obtained by particles containing each RNA individually. The production of both interferon-alpha and interferon-beta by human immune cells is higher using the chimeric particles than when using respectively ssRNA- or dsRNA-containing particles. Thus, there is a synergy between the different TLRs and/or different cell types resulting in some kind of immunobiological resonance that is of upmost interest for an immunomodulating drug.

SUMMARY OF THE INVENTION

In a first aspect, the present invention relates to a particle comprising single stranded RNA (ssRNA) and double stranded RNA (dsRNA), wherein the RNA in the particle is associated with at least one cationic agent.

In one embodiment, the particle has a diameter in the range of from about 50 nm to about 1000 nm.

In one embodiment, the at least one cationic agent forms a complex with and/or encloses said RNA. In one embodiment, the at least one cationic agent is comprised in a vesicle enclosing the RNA, wherein the vesicle preferably is a multilamellar vesicle, an unilamellar vesicle, or a mixture thereof. In one embodiment, the vesicle is a liposome, preferably a cationic liposome. In one embodiment, the liposome comprises a phospholipid such as phosphatidylcholine and/or a sterol such as cholesterol.

In one embodiment, the at least one cationic agent comprises a polycationic compound. In one embodiment, the at least one cationic agent comprises at least one agent selected from the group consisting of an RNA-complexing lipid, an RNA complexing polymer and an RNA-complexing peptide or protein. In one embodiment, the at least one cationic agent comprises at least one agent selected from the group consisting protamine, polyethyleneimine, a poly-L-lysine, a poly-L-arginine or a histone.

In one embodiment, the at least one cationic agent comprises or consist of protamine. In this embodiment, the protamine:RNA (ssRNA+dsRNA) weight ratio is from 16:1 to 1:2, more preferably from 4:1 to 1:2. A mass ratio of protamine to the total RNA (ssRNA+dsRNA) of 1 to 1 or higher (i.e. more protamine than total RNA) is preferred since it results in an optimal immunostimulation.

In one embodiment, the ssRNA contains at least one U nucleotide and/or at least one G nucleotide. In one embodiment, the ssRNA is an oligonucleotide of from 6 to 100 nucleotides, preferably an oligonucleotide having the sequence according to SEQ ID NO: 1. In one embodiment, the ssRNA is an mRNA of from 50 to 10,000 nucleotides.

In one embodiment, the dsRNA comprises two RNA molecules capable to fully or partially hybridize together. In one embodiment, the strands of the dsRNA are in average from 6 to 8000 nucleotides in length although the benefits of the present invention are independent of the ssRNA and dsRNA lengths. In one embodiment, the dsRNA is polyinosinic-polycytidylic acid (poly(I:C))

The particle of the invention may comprise a ligand for site specific targeting such as an antibody. The ligand may be capable of binding to a disease-associated antigen such that the particle when administered accumulates at a diseased organ or tissue characterized by cells expressing the disease-associated antigen and preferably being characterized by association of the disease-associated antigen with their cell surface, e.g. the disease-associated antigen is a transmembrane protein. The disease-associated antigen may be a tumor-associated antigen and is preferably associated with the surface of a diseased cell such as a tumor cell but preferably not with the surface of a healthy cell. Preferably the ligand for site specific targeting binds to an extracellular portion of the disease-associated antigen.

Particles of the invention when contacted with appropriate cells or administered to a subject are capable of inducing interferon-alpha and interferon-beta. Thus, the particles according to the invention are particularly useful as an immunostimulating medicament.

The present invention also relates to a pharmaceutical composition comprising (the) particle(s) of the invention and optionally one or more pharmaceutically acceptable carriers, diluents and/or excipients. The pharmaceutical composition of the invention may further comprise at least one adjuvant such as an oil and/or at least one antigen.

The present invention also relates to a method for stimulating the immune system of a subject comprising administering to the subject an effective amount of a pharmaceutical composition of the present invention. The stimulation of the immune system preferably involves the stimulation of one or more of TLR-7, TLR-8 and TLR-3, preferably TLR-7 and TLR-3, more preferably TLR-7, TLR-8 and TLR-3. Furthermore, the stimulation of the immune system preferably involves increasing the level of interferons, preferably interferon-alpha and/or interferon-beta.

The pharmaceutical composition of the present invention may be co-administered with a further immunomodulating agent which may be selected from the group consisting of chemotherapeutic drugs, chloroquine, anti-CTLA-4 or anti-regulatory T-cell reagents and/or at least one antigen. The immunomodulating agent and/or the at least one antigen may be administered prior to, simultaneously with or after administration of the pharmaceutical composition of the present invention. If the immunomodulating agent and/or the at least one antigen is administered simultaneously with administration of the pharmaceutical composition of the present invention, the immunomodulating agent and/or the at least one antigen may be comprised in the pharmaceutical composition of the present invention.

In a further aspect, the present invention provides an ex vivo method for stimulating immune cells by contacting the immune cells with particles of the present invention. These stimulated immune cells can be transferred into a subject such as the subject from whom the immune cells were obtained to stimulate the immune system of the subject. In one embodiment, suitable immune cells are isolated from a subject and are treated in vitro via adding to the isolated immune cells an effective amount of particles of the present invention, and the stimulated immune cells are re-introduced into the subject. Suitable immune cells for such ex vivo treatment include but are not limited to dendritic cells and natural killer (NK) cells.

In a further aspect, the present invention relates to a method for the production of particles as defined herein, which method comprises the steps of:
(a) providing an aqueous solution of ssRNA;
(b) providing an aqueous solution of dsRNA;
(c) providing an aqueous solution of protamine; and
(d) combining the solutions obtained in steps (a) and (b) and mixing it with the solution obtained in (c).

Preferably, the above steps (a) and (b) are performed by resuspending an appropriate amount of dried RNA in an aqueous solution containing 0 to 125 mM electrolytes, preferably containing less than 100 mM, more preferably less than 50 mM and, in particular, less than 25 mM electrolytes.

Preferably, the above step (c) is carried out by diluting a solution of protamine, preferably an aqueous isotonic stock solution of protamine, preferably containing 1000 ("protamine 1000") to 5000 ("protamine 5000") heparin-neutralizing units per ml with a solution containing 0 to 125 mM electrolytes, preferably containing less than 100 mM, more preferably less than 50 mM and, in particular, less than 25 mM electrolytes. For example, protamine 1000 and 5000 stock solutions are commercially available from Valeant Pharmaceuticals International, Aliso Viejo, Calif., USA, under the trademarks Valeant® 1000 and 5000, respectively.

In one embodiment, particles of the present invention comprising protamine, ssRNA and dsRNA are prepared by diluting all three ingredients to less than 5 mg/ml, preferably to 1 mg/ml or less in an aqueous solution containing 0 to 125 mM electrolytes, preferably in pure water. In one embodiment, (i) protamine is formulated as a 1 mg/ml solution by diluting a pharmaceutical isotonic solution of at least 10 mg/ml (protamine 5000) with pure water and (ii) a mixture of equal mass amounts of dsRNA and ssRNA is formulated as a 1 mg/ml solution by diluting dried RNA pellets in pure water and (iii) these preparation are mixed. It has been demonstrated according to the invention that such procedure forms homogenous particles.

In one embodiment, the method according to the present invention comprises the following steps:
(a) providing an aqueous solution of ssRNA at less than 5 mg/ml in pure water;
(b) providing an aqueous solution of dsRNA at less than 5 mg/ml in pure water
(c) providing an aqueous solution of protamine at less than 5 mg/ml by diluting an aqueous isotonic stock solution containing 5000 heparin-neutralizing units of protamine per ml with pure water;
(d) combining the solutions obtained in steps (a) and (b), and
(e) combining the solutions obtained in steps (d) and (c).

BRIEF DESCRIPTION OF THE DRAWINGS

Other objects, advantages and novel features of the present invention will become apparent from the following detailed description when considered in conjunction with the accompanying drawings.

RNA and protamine were diluted to 1 mg/ml using pure water. 5 micrograms of RNA (ssRNA:RNA18 or dsRNA or a mixture of 2.5 micrograms of ssRNA with 2.5 micrograms of dsRNA) were mixed with 10 micrograms of protamine, the solutions were centrifuged and the pellets were resuspended in 10 microliters of water containing 0.5% sodium dodecyl sulfate (SDS) and 2 microliters of 10 mg/ml proteinase K were added to digest protamine. The formulations were separated on a 2% native agarose gel.

The gel on the left shows an example of the results obtained with HMW dsRNA and the gel on the right shows an example of the results obtained with LMW dsRNA. "R18" is ssRNA alone, "HMW" is high molecular weight dsRNA, "LMW" is low molecular weight dsRNA, "R18+HMW" is a mixture of RNA18 and HMW dsRNA, "R18+LMW" is a mixture of RNA18 and LMW dsRNA. It is demonstrated that both ssRNA and dsRNA alone or mixed together get trapped in the particles (found in the pellets).

Figure 2:
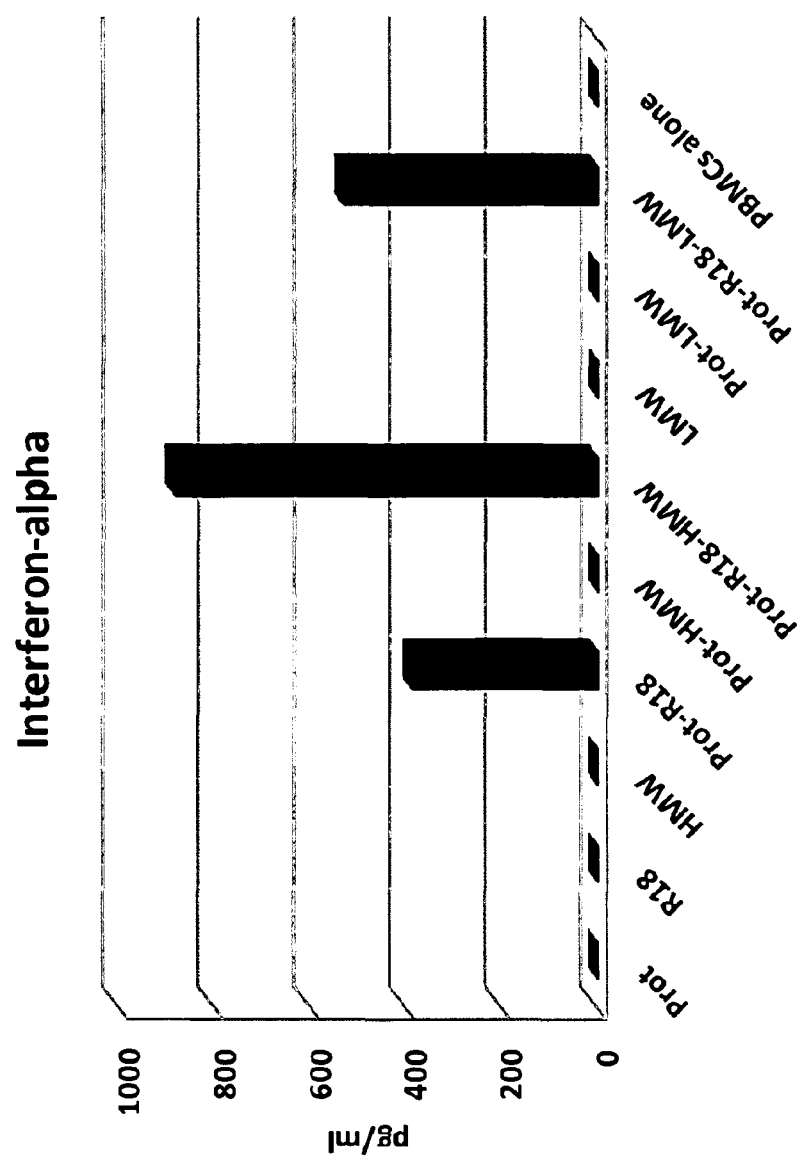

FIG. 2: Immunostimulation capacity of protamine/ssRNA/dsRNA particles as reflected by interferon-alpha production in PBMCs from a healthy human donor.

Two hundred microliters (1 million of cells) of a human Peripheral Blood Mononuclear Cells (PBMCs obtained by centrifugation of fresh blood on a ficoll solution) preparation were added on top of one of the following: 4 micrograms of protamine ("Prot"); 2 micrograms of ssRNA, oligonucleotide RNA18 ("R18"); 2 micrograms of High Molecular Weight dsRNA ("HMW"); 4 micrograms of protamine mixed with 2 micrograms of ssRNA ("Prot-R18"); 4 micrograms of protamine mixed with 2 micrograms of High Molecular Weight dsRNA ("Prot-HMW"); 4 micrograms of protamine mixed with 1 microgram of ssRNA and 1 microgram of High Molecular Weight dsRNA ("Prot-R18-HMW"); 2 micrograms of Low Molecular Weight dsRNA ("LMW"); 4 micrograms of protamine mixed with 2 micrograms of Low Molecular Weight dsRNA ("Prot-LMW"); 4 micrograms of protamine mixed with 1 microgram of ssRNA and 1 microgram of Low Molecular Weight dsRNA ("Prot-R18-LMW"). As negative control, PBMCs were cultured alone.

Chimeric particles containing ssRNA and dsRNA (high or low molecular weight) are immunostimulating. In general, interferon-alpha production was superior using stimulation with chimeric particles (ssRNA+dsRNA) than when using particles containing only ssRNA. The addition of protamine on dsRNA was not increasing (and rather decreasing the minimal interferon-alpha induction observed in some experiments by naked dsRNA) its immunostimulating activity as judged by interferon-alpha production.

Figure 3:
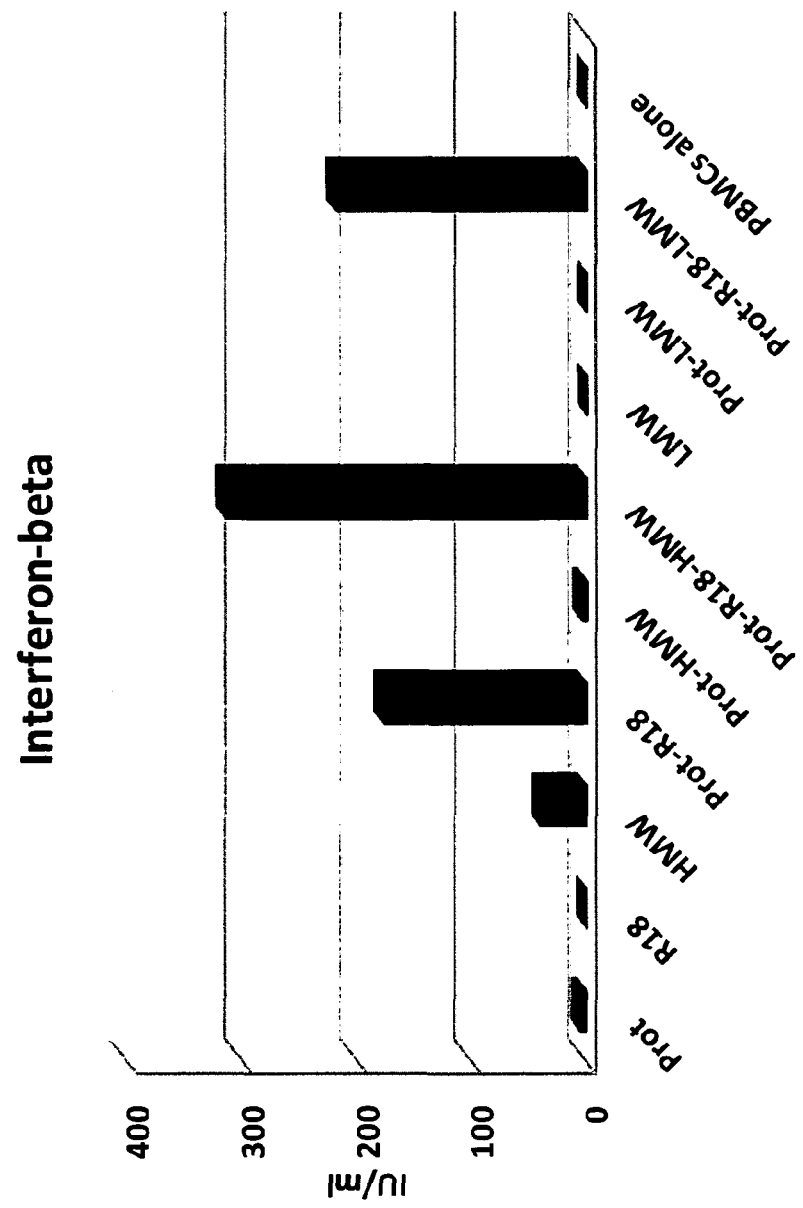

FIG. 3: Immunostimulation capacity of protamine/ssRNA/dsRNA particles as reflected by interferon-beta production in PBMCs from a healthy human donor.

Two hundred microliters (1 million of cells) of a human PBMC preparation were added on top of one of the following: 4 micrograms of protamine ("Prot"); 2 micrograms of ssRNA, oligonucleotide RNA18 ("R18"); 2 micrograms of High Molecular Weight dsRNA ("HMW"); 4 micrograms of protamine mixed with 2 micrograms of ssRNA ("Prot-R18"); 4 micrograms of protamine mixed with 2 micrograms of High Molecular Weight dsRNA ("Prot-HMW"); 4 micrograms of protamine mixed with 1 microgram of ssRNA and 1 microgram of High Molecular Weight dsRNA ("Prot-R18-HMW"); 2 micrograms of Low Molecular Weight dsRNA ("LMW"); 4 micrograms of protamine mixed with 2 micrograms of Low Molecular Weight dsRNA ("Prot-LMW"); 4 micrograms of protamine mixed with 1 microgram of ssRNA and 1 microgram of Low Molecular Weight dsRNA ("Prot-R18-LMW"). As negative control, PBMCs were cultured alone.

Chimeric particles containing ssRNA and dsRNA (high or low molecular weight) are immunostimulating. In general, interferon-beta production was superior using stimulation with chimeric particles (ssRNA+dsRNA) than when using particles containing only ssRNA. The addition of protamine on dsRNA was not increasing but rather decreasing its immunostimulating activity as judged by interferon-beta production. Thus, it is unexpected that dsRNA increases the immunostimulating activity when incorporated in ssRNA-Protamine particles.

Figure 4:
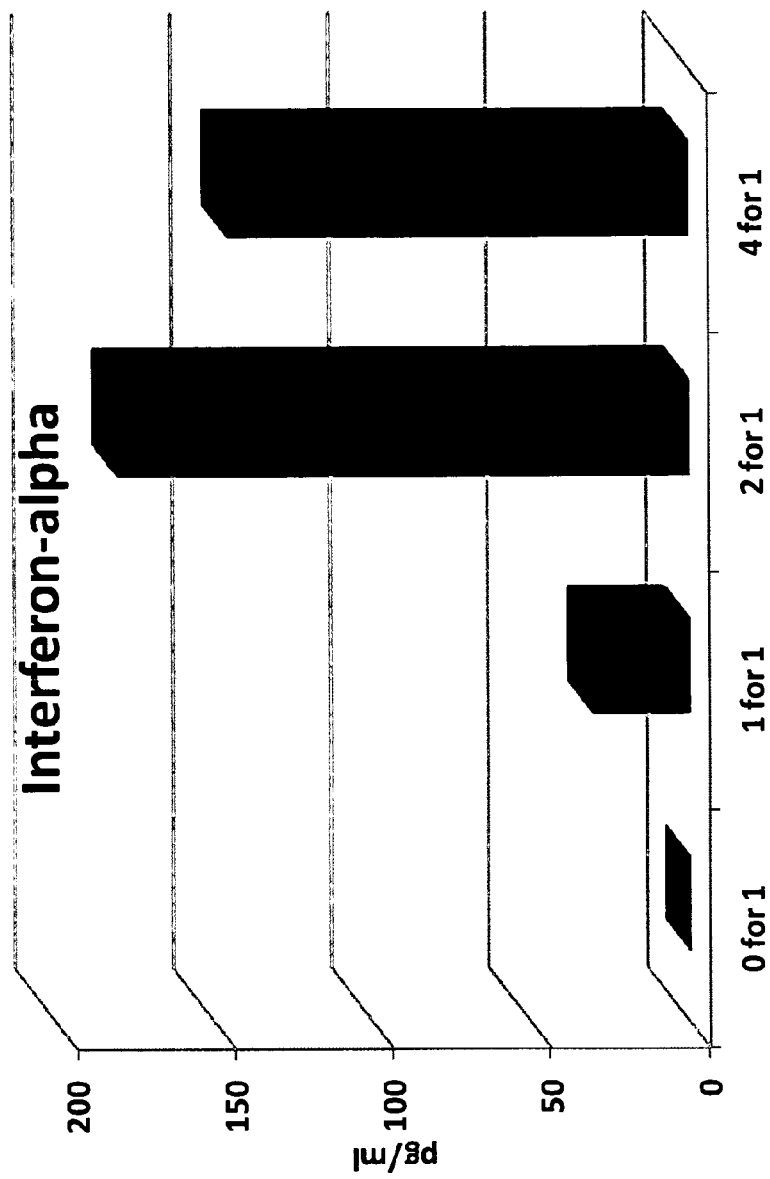

FIG. 4: Immunostimulation capacity of protamine/ssRNA/dsRNA particles as reflected by interferon-alpha production in PBMCs from a healthy human donor using different protamine/total RNA ratios.

Two hundred microliters (1 million of cells) of a PBMC preparation were added on top of one of the following: 1 microgram of ssRNA (RNA18) and 1 microgram of High Molecular Weight dsRNA ("0 for 1"); 2 micrograms of protamine mixed with 1 microgram of ssRNA (RNA18) and 1 microgram of High Molecular Weight dsRNA ("1 for 1"); 4 micrograms of protamine mixed with 1 microgram of ssRNA (RNA18) and 1 microgram of High Molecular Weight dsRNA ("2 for 1"); 8 micrograms of protamine mixed with 1 microgram of ssRNA (RNA18) and 1 microgram of High Molecular Weight dsRNA ("4 for 1")

Addition of protamine on a mixture of ssRNA and dsRNA allows stimulation of immune cells at protamine-RNA mass ratios from 1-1 up to 4-1.

Figure 5:
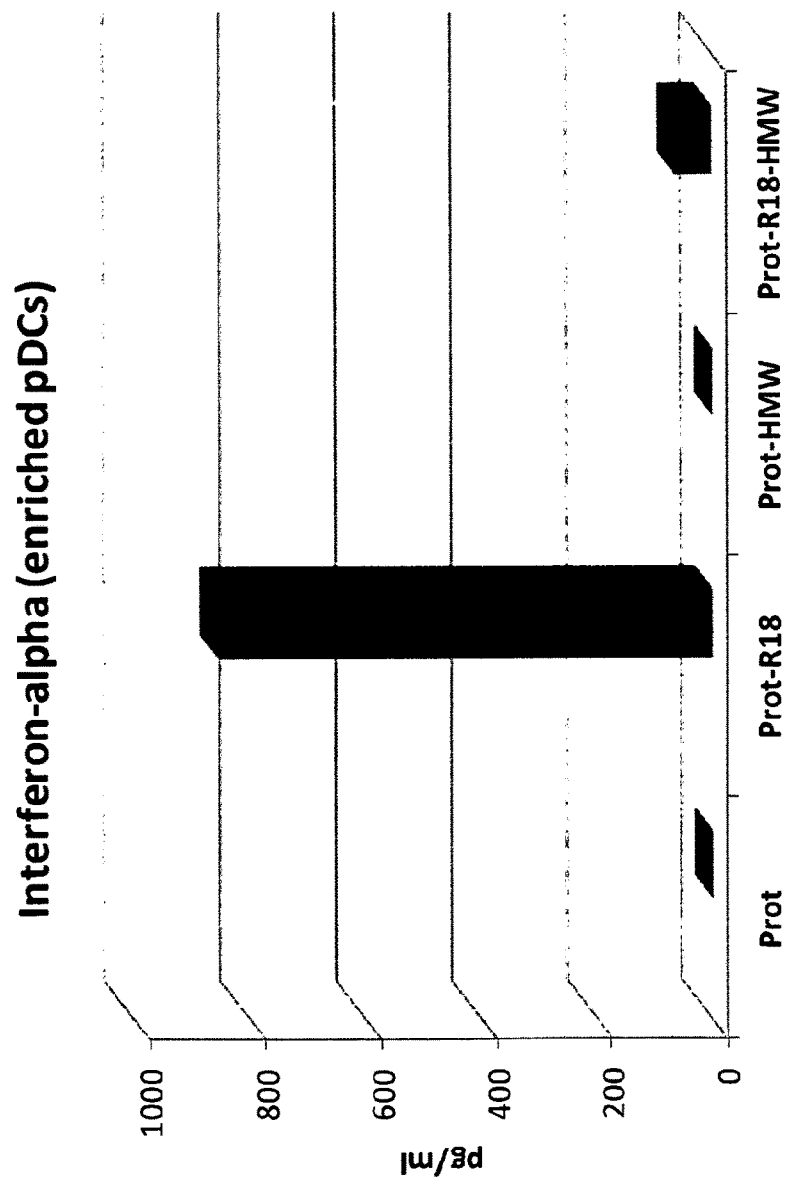

FIG. 5: Synergistic immunostimulating activity of ssRNA and dsRNA as far as interferon-alpha production by plasmacytoid DC is concerned depends on third cell type(s).

pDCs (BDCA-2 positive) were mixed with one of the following: 2 micrograms of ssRNA (RNA18) with 8 micrograms of protamine (both reagents at 1 mg/ml diluted in pure water). ("Prot-R18"); 2 micrograms of dsRNA (high molecular weight poly (I:C)) with 8 micrograms of protamine (both reagents at 1 mg/ml diluted in pure water). ("Prot-HMW"); 1 microgram of ssRNA (RNA18) and 1 microgram of dsRNA (poly(I:C)) with 8 micrograms of protamine (all reagents at 1 mg/ml diluted in pure water) ("Prot-R18-HMW"). The negative control is the same pDC-enriched cell population cultured in the presence of 8 micrograms of protamine ("Prot").

The high interferon-alpha production in PBMCs induced by chimeric particles containing 1 microgram of ssRNA and 1 microgram of dsRNA is not obtained in enriched pDCs cell suspension. Protamine-based particles containing 2 micrograms of ssRNA are superior in stimulating sorted pDCs compared to chimeric particles containing 1 microgram of ssRNA and 1 microgram of dsRNA. Thus, the capacity of the protamine/ssRNA/dsRNA particles to induce high interferon-alpha production in PBMC depends probably on the stimulation by those chimeric particles of other cells in addition to pDCs.

Figure 6:
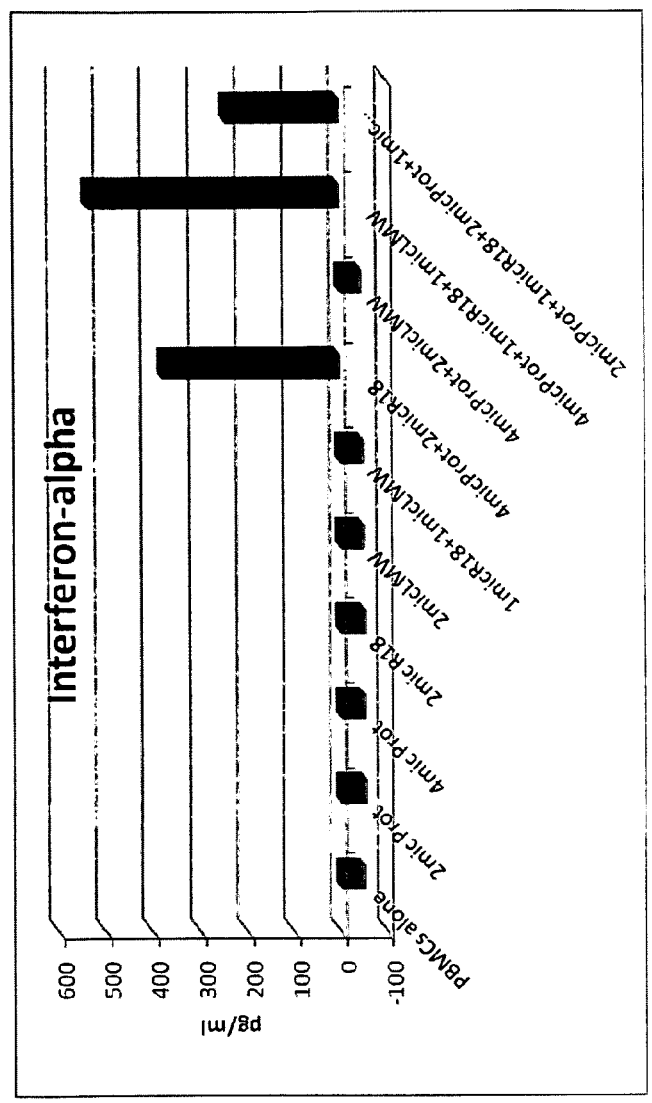

FIG. 6: Immunostimulating capacity of protamine/ssRNA/dsRNA particles versus protamine/ssRNA mixed with protamine/dsRNA as reflected by interferon-alpha production.

Two hundred microliters (1 million of cells) of a PBMC preparation were added on top of one of the following: 2 or 4 micrograms of protamine ("2micProt" and "4micProt", respectively); 2 micrograms of ssRNA, oligonucleotide RNA18 ("2micR18"); 2 micrograms of Low Molecular Weight dsRNA ("2micLMW"); 1 microgram of ssRNA, oligonucleotide RNA18 mixed with 1 microgram of Low Molecular Weight dsRNA ("1micR18"1micLMW"); 4 micrograms of protamine mixed with 2 micrograms of ssRNA ("4micProt+2micR18"); 4 micrograms of protamine mixed with 2 micrograms of Low Molecular Weight dsRNA ("4micProt+2micLMW"); 4 micrograms of protamine mixed with 1 microgram of R18 combined with 1 microgram of Low Molecular Weight dsRNA ("4micProt+1micR18+1micLMW"); A mixture of two independent formulations ("2micProt+1micR18+2micProt+1micLMW"): the first one containing 2 microliters of protamine mixed with 1 microgram of single stranded RNA and the second one containing 2 microliters of protamine mixed with 1 microgram of dsRNA. As negative control, PBMCs were cultured alone.

Chimeric particles containing both ssRNA and dsRNA are more immunostimulating than a mixture of two formulations containing protamine+ssRNA and protamine+dsRNA.

DETAILED DESCRIPTION OF THE INVENTION

In the following, definitions will be provided which apply to all aspects of the present invention.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The present inventor surprisingly observed that particles containing single stranded RNA (ssRNA) and double stranded RNA (dsRNA) within the same particle can be formed. They have superlative immunostimulation capacities as compared to particles containing either ssRNA or dsRNA. The superlative features of the chimeric particles probably relies on cross talk between cells stimulated by the particles through TLR-3 and/or TLR-7 and/or TLR-8. For generating highly immunostimulating particles the ssRNA molecules are preferably at least 10 residues in length and contain U-residues and/or the dsRNA molecules are preferably between 10 and 8000 residues in average length and are preferably made of poly (I:C). Furthermore, protamine is preferred as cationic carrier agent in the particles and the mass ratio of protamine to total RNA is preferably at least 0.5 (preferably not more than twice more RNA than protamine). In preferred embodiments this ratio is 1 or higher (most preferred the same mass amount of protamine and total RNA or more protamine than total RNA is used), 2 or higher, 4 or higher and preferably up to 16, more preferably up to 8.

A preferred procedure for the preparation of particles of the invention containing protamine as the cationic agent comprises the steps of diluting protamine, ssRNA and dsRNA at concentrations of less than approx. 5 mg/ml, at best at 1 mg/ml or less using pure water or low salt solution (preferably less than 125 mM electrolytes), mixing the two RNA solutions and then adding protamine preferably in mass excess compared to the whole RNA content.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the invention, "ssRNA" means single-stranded RNA and includes mRNA, tRNA, rRNA, snRNAs, and other ssRNAs. ssRNA may contain self-complementary sequences that allow parts of the RNA to fold and pair with itself to form double helices. According to the invention preferred as ssRNA are synthetic oligonucleotides of 6 to 100, preferably 10 to 50, in particular 15 to 30 or 15 to 20 nucleotides or messenger RNA (mRNA) of more than 50 nucleotides, preferably of 50 to 10,000, preferably 100 to 5000, in particular 200 to 1000 nucleotides.

According to the present invention, the term "mRNA" means "messenger-RNA" and relates to a "transcript" which may be generated by using a DNA template and may encode a peptide or protein. Typically, an mRNA comprises a 5'-UTR, a protein coding region, and a 3'-UTR. In the context of the present invention, mRNA may be generated by in vitro transcription from a DNA template. The in vitro transcription methodology is known to the skilled person. For example, there is a variety of in vitro transcription kits commercially available.

According to the invention, "dsRNA" means double-stranded RNA and is RNA with two partially or completely complementary strands. The size of the strands may vary from 6 nucleotides to 10000, preferably 10 to 8000, in particular 200 to 5000, 200 to 2000 or 200 to 1000 nucleotides. According to the invention preferred dsRNA is polyinosinic-polycytidylic acid (poly(I:C)), a synthetic analog of dsRNA. Poly(I:C) is composed of a strand of poly(I) annealed to a strand of poly(C).

The dsRNA is preferably a fully or partially (interrupted) pair of RNA hybridized together. It can be made for example by mixing polyinosinic and polycytidylic acid RNA molecules. It also can be made by mixing defined fully or partially pairing non-homopolymeric RNA strands.

There is no specific ribonucleotide sequence requirement for the ssRNA and dsRNA molecules to be suitable for preparing an immunostimulatory particle according to the present invention. However, it is not excluded that certain ssRNA or dsRNA sequences would provide best biological activities. However, preferably, the ssRNA component should contain at least 25% uridine residues.

Most preferably, the ssRNA is an oligonucleotide that has the following sequence (written 5' to 3'): 18merU: AGU-GUUAUUCUUGUAUGG (SEQ ID NO: 1).

According to the invention, the stability of RNA may be modified as required. For example, RNA may be stabilized by one or more modifications having stabilizing effects on RNA.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap ($m^7G$). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA.

Of course, if according to the present invention it is desired to decrease stability of RNA, it is possible to modify RNA so as to interfere with the function of elements as described above increasing the stability of RNA.

According to the present invention, RNA may be obtained by chemical synthesis or by in vitro transcription of an appropriate DNA template. The promoter for controlling transcription can be any promoter for any RNA polymerase. Particular examples of RNA polymerases are the T7, T3, and SP6 RNA polymerases. A DNA template for in vitro transcription may be obtained by cloning of a nucleic acid, in particular cDNA, and introducing it into an appropriate vector for in vitro transcription. The cDNA may be obtained by reverse transcription of RNA. Preferably cloning vectors are used for producing transcripts which generally are designated transcription vectors.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

Particles of the present invention preferably have a defined average size (diameter) of about 50 to about 1000 nm, preferably about 100 nm to about 700 nm, more preferably about 200 nm to about 500 nm.

The average "size" of the particles is generally the "design size" or intended size of the particles prepared according to an established process. Size may be a directly measured dimension, such as average or maximum diameter, or may be determined by an indirect assay such as a filtration screening assay. Direct measurement of particle size is typically carried out by dynamic light scattering. As minor variations in size arise during the manufacturing process, a variation up to 40% of the stated measurement is acceptable and considered to be within the stated size. Alternatively, microcarrier size may be determined by filtration screening assays. For example, a particle preparation is less than a stated size, if at least 97% of the particles pass through a "screen-type" filter of the stated size.

Cationic agents contemplated for use as carriers in the present invention include any substances or vehicles with which RNA can be associated, e.g. by forming complexes with the RNA or forming vesicles in which the RNA is enclosed or encapsulated, preferably resulting in increased stability of the RNA compared to naked RNA.

The carriers useful according to the invention include lipid-containing carriers such as cationic lipids, liposomes and micelles, cationic polymers such as DEAE dextran or polyethyleneimine and nanoparticles.

Cationic lipids may form complexes with negatively charged nucleic acids. Any cationic lipid may be used according to the invention. Cationic lipids and cationic polymers can be used to complex nucleic acids, thereby forming so-called lipoplexes and polyplexes, respectively, and these complexes have been shown to deliver nucleic acids into cells.

Liposomes are microscopic lipidic vesicles often having one or more bilayers of a vesicle-forming lipid, such as a phospholipid, and are capable of encapsulating a drug. Different types of liposomes may be employed in the context of the present invention, including, without being limited thereto, multilamellar vesicles (MLV), small unilamellar vesicles (SUV), large unilamellar vesicles (LUV), sterically stabilized liposomes (SSL), multivesicular vesicles (MV), and large multivesicular vesicles (LMV) as well as other bilayered forms known in the art. The size and lamellarity of the liposome will depend on the manner of preparation and the selection of the type of vesicles to be used will depend on the preferred mode of administration. Preferred injectable liposomes are those in the size range of 10-500, 20-400, 50-200, 50-150, 50-120, 50-100, or 50-90 nm in diameter. Cationic liposomes are structures that are made of positively charged lipids and are increasingly being used in gene therapy due to their favourable interactions with negatively charged nucleic acids and cell membranes. Cationic liposomes are also known as cationic lipoplexes. Liposomes should not be confused with micelles and reverse micelles composed of monolayers. The lipid assembly may be combined with stabilizers. Non-limiting examples of stabilizers include cholesterol and similar membrane active sterols, lipopolymers such as PEGylated lipids.

Formation of liposomes is not a spontaneous process. Lipid vesicles are formed when phospholipids such as lecithin are placed in water and consequently form one bilayer or a series of bilayers, each separated by water molecules, once enough energy is supplied. Liposomes may be formed using standard methods such as the reverse evaporation method (REV), the dehydration-rehydration method (DRV), sonication or other suitable methods. Liposomes can be created, for example, by sonicating phospholipids in water. Low shear rates create multilamellar liposomes, which have many layers. Continued high-shear sonication tends to form smaller unilamellar liposomes. In this technique, the liposome contents are the same as the contents of the aqueous phase. Sonication is generally considered a "gross" method of preparation as it can damage the structure of the drug to be encapsulated. Newer methods such as extrusion and Mozafari method are employed to produce materials for human use.

After liposome formation, the liposomes can be sized to obtain a population of liposomes having a substantially homogeneous size range, typically between about 10 and 500 nm.

Any suitable liposome-forming material can be used in the present liposomes.

The liposomes can include a vesicle-forming lipid derivatized with a hydrophilic polymer to form a surface coating of hydrophilic polymer chains on the liposome surface.

In accordance with one embodiment of the invention the particles of the invention comprise on their outer surface a targeting agent which can selectively or preferably deliver the particles to a target cell population, and/or to a target organ or tissue. For example, liposomes bearing ligands can target receptors expressed on diseased cells. This ligand-binding promotes efficient drug uptake into cells and enhances efficacy. One targeting means which has been explored employs antibodies attached covalently or through electrostatic interactions to particle surfaces.

According to the invention, protamine is preferred as cationic carrier agent. The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the invention, the term "protamine" as used herein is meant to comprise any protamine amino acid sequence obtained or derived from native or biological sources including fragments thereof and multimeric forms of said amino acid sequence or fragment thereof. Furthermore, the term encompasses (synthesized) polypeptides which are artificial and specifically designed for specific purposes and cannot be isolated from native or biological sources.

The protamine used according to the present invention can be sulfated protamine or hydrochloride protamine. In a preferred embodiment, the protamine source used for the production of the particles of the invention is protamine 5000 which contains protamine at more than 10 mg/ml (5000 heparin-neutralizing units per ml) in an isotonic salt solution and which is diluted as set forth above.

The particles of the invention preferably have a protamine:total RNA weight ratio from 16:1 to 1:2, preferably from 8:1 to 1:2, more preferably from 4:1 to 1:2. In one embodiment, the lower range limit of the protamine:total RNA weight ratio is 1:1, preferably 2:1. The ssRNA:dsRNA ratio can largely vary and be between 100:1 to 1:100, preferably 10:1 to 1:10, more preferably 1:1.

The term "peptide" according to the invention comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" preferentially refers to large peptides, preferably to peptides with more than 100 amino acid residues, but in general the terms "peptide" and "protein" are synonyms and are used interchangeably herein.

In the context of the present invention the terms "salt(s)" and "electrolyte(s)" are used interchangeably and mean a compound that at least partially dissociates into its respective counter ions in water.

According to the present invention, the term "mM electrolytes" means the concentration in $10^{-3}$ mol per liter of the sum of all electrolytes (including inorganic salts such as NaCl, KCl, NaH$_2$PO$_4$, Na$_2$HPO$_4$, KH$_2$PO$_4$, K$_2$HPO$_4$, MgCl$_2$, MnCl$_2$, Na$_2$SO$_4$, K$_2$SO$_4$, MgSO$_4$ and salts such as Tris-HCl, EDTA, Hepes, etc.) in the solutions used to resuspend or to dilute the ssRNA and dsRNA stock solutions and in the solutions used to dilute a protamine stock solution (such as protamine 1000 or 5000) before mixing the components (i.e. (a), (b) and (c) as defined above).

It should be noted that, once the particles of the present invention are formed, the specific salt (or electrolyte) concentration conditions used for preparing the particles need not to be further maintained. Thus, the particles can be further processed, e.g. eventually recovered by centrifugation and diluted, dissolved or dispersed in a medium, preferably a pharmaceutically acceptable excipient, vehicle and/or diluent, in particular in an isotonic medium such as saline, Ringer or Ringer Lactate solution.

It is demonstrated herein that particles of the present invention have a strong immunostimulatory effect and are able to induce a nonspecific general activation of the immune system. Accordingly, the present invention provides a method of immunostimulation, in particular for stimulating an immune response in a subject, preferably a mammal, especially a human, comprising the administration of an effective amount of a pharmaceutical composition according to the invention.

The particles and pharmaceutical composition of the present invention are useful to activate or strengthen the immunity in certain disease states, in particular in the case of chronic diseases, such as cancer or infectious diseases, in particular persistent virus infections. Thus, the particles and pharmaceutical composition of the present invention are useful in the treatment of said disease states. The particles and pharmaceutical composition of the present invention are particularly suitable for inducing production, or increasing the level of interferons, in particular interferon-alpha and/or interferon-beta. Thus, the particles and pharmaceutical composition of the present invention may be used to supplement interferon-alpha treatment and/or interferon-beta treatment, or to increase interferon-alpha and/or interferon-beta in a subject.

According to the invention, the term "disease" refers to any pathological state, including cancer diseases. Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e. a swelling or lesion formed by an abnormal growth of cells (called neoplastic cells or tumor cells), but some, like leukemia, do not. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Examples of cancers treatable with the particles and pharmaceutical composition of the present invention include malignant melanoma, all types of carcinoma (colon, renal cell, bladder, prostate, non-small cell and small cell lung carcinoma, etc.), lymphomas, sarcomas, blastomas, gliomas, etc.

Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

Lymphoma and leukemia are malignancies derived from hematopoietic (blood-forming) cells.

A sarcoma is a cancer that arises from transformed cells in one of a number of tissues that develop from embryonic mesoderm. Thus, sarcomas include tumors of bone, cartilage, fat, muscle, vascular, and hematopoietic tissues.

Blastic tumor or blastoma is a tumor (usually malignant) which resembles an immature or embryonic tissue. Many of these tumors are most common in children.

A glioma is a type of tumor that starts in the brain or spine. It is called a glioma because it arises from glial cells. The most common site of gliomas is the brain.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e. a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

Examples of infectious diseases treatable with the particles and pharmaceutical composition of the present invention include viral infectious diseases, such as AIDS (HIV), hepatitis A, B or C, herpes, herpes zoster (chicken-pox), German measles (*rubella* virus), yellow fever, dengue etc. flaviviruses, influenza viruses, hemorrhagic infectious diseases (Marburg or Ebola viruses), bacterial infectious diseases, such as Legionnaire's disease (*Legionella*), gastric ulcer (*Helicobacter*), cholera (*Vibrio*), infections by *E. coli*, Staphylococci, *Salmonella* or Streptococci (tetanus); infections by protozoan pathogens such as malaria, sleeping sickness, leishmaniasis; toxoplasmosis, i.e. infections by *Plasmodium, Trypanosoma, Leishmania* and *Toxoplasma*; or fungal infections, which are caused e.g. by *Cryptococcus neoformans, Histoplasma capsulatum, Coccidioides immitis, Blastomyces dermatitidis* or *Candida albicans*).

The particles and pharmaceutical composition of the present invention are also useful in treating allergies.

The particles and pharmaceutical composition of the present invention can also be used in conjunction with another therapeutic agent which can be administered prior to, simultaneously with or after administration of the particles or pharmaceutical composition of the present invention. Such therapeutic agents include chemotherapeutic drugs for cancer patients, e.g. gemcitabine, etopophos, cis-platin, carbo-platin, antiviral agents, anti-parasite agents or an anti-bacterial agents and, if administered simultaneously with the particles of the present invention, may be present in a pharmaceutical composition of the present invention.

In particular, the particles and pharmaceutical composition of the present invention can also be used in conjunction with an immunotherapeutic agent, preferably an immunotherapeutic agent inducing or effecting a targeted, i.e. specific, immune reaction. Such immunotherapeutic agents include agents directed against a disease-associated antigen such as therapeutic antibodies or agents inducing an immune response direct against a disease-associated antigen or cells expressing a disease-associated antigen. Useful immunotherapeutic agents include proteins or peptides inducing a B cell or T cell response against the disease-associated antigen or cells expressing the disease-associated antigen. These proteins or peptides may comprise a sequence essentially corresponding to or being identical to the sequence of the disease-associated antigen or one or more fragments thereof. In one embodiment, the protein or peptide comprises the sequence of an MHC presented peptide derived from the disease-associated antigen. Instead of administering the protein or peptide it is also possible to administer nucleic acid, preferably mRNA, encoding the protein or peptide. Accordingly, the pharmaceutical composition of the present invention may be used in genetic vaccination, wherein an immune response is stimulated by introduction into a subject a suitable nucleic acid molecule (DNA or mRNA) which codes for an antigen or a fragment thereof.

If the nucleic acid to be administered as therapeutic agent is mRNA it can be present in the particles of the invention in addition to the ssRNA and dsRNA or it can form at least part of the ssRNA present in the particles of the invention.

In one embodiment, a disease-associated antigen is a tumor-associated antigen. In this embodiment, the particles and pharmaceutical composition of the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunisation with intact or substantially intact tumor-associated antigen or fragments thereof such as MHC class I and class II peptides or nucleic acids, in particular mRNA, encoding such antigen or fragment makes it possible to elicit a MHC class I and/or a class II type response and thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I—presented peptides directly or by transfection with nucleic acids encoding tumor antigens or tumor antigen peptides in vitro and administered to a patient.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e. in a healthy subject, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a cancer cell and is preferably not or only rarely expressed in normal tissues. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor-associated antigen is identical between the tumor-associated antigen which is expressed in normal tissues and the tumor-associated antigen which is expressed in cancer tissues. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Further examples for antigens that may be useful in the present invention are p53, ART-4, BAGE, beta-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MCI R, Myosin/m, MUC1, MUM-1, -2, -3, NA88-A, NF1, NY-ESO-1, NY-BR-1, p190 minor BCR-abL, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

The pharmaceutical composition of the present invention may take the form of a vaccine preparation comprising the particles of the invention and at least one antigen such as an antigen as discussed above or an immunogenic fragment thereof, or a nucleic acid, in particular RNA, encoding said antigen or fragment.

An "antigen" is to be understood as meaning any structure which can cause the formation of antibodies and/or the activation of a cellular immune response. Examples of antigens are polypeptides, proteins, cells, cell extracts, carbohydrates/polysaccharides, polysaccharide conjugates, lipids, and glycolipids. These antigens may be tumor antigens or viral, bacterial, fungal and protozoological antigens or allergens. The term "antigen" also includes derivatized antigens as secondary substance which becomes antigenic—and sensitizing—only through transformation (e.g., intermediately in the molecule, by completion with body protein), and conjugated antigens which, through artificial incorporation of atomic groups (e.g., isocyanates, diazonium salts), display a new constitutive specificity. The antigen may be present in the vaccine according to the invention in the form of a hapten coupled to a suitable carrier. Suitable carriers are known to those ordinarily skilled in the art and include e.g. human serum albumin (HSA), polyethylene glycols (PEG). The hapten may be coupled to the carrier by processes well-known in the prior art, e.g. in the case of a polypeptide carrier via an amide bond to a Lys residue.

By "treat" is meant to administer a compound or composition as described herein to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e. increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

The term "immunotherapy" relates to a treatment preferably involving a specific immune reaction and/or immune effector function(s).

The term "immunization" or "vaccination" describes the process of treating a subject for therapeutic or prophylactic reasons.

The term "subject" relates to mammals. For example, mammals in the context of the present invention are humans, non-human primates, domesticated animals such as dogs, cats, sheep, cattle, goats, pigs, horses etc., laboratory animals such as mice, rats, rabbits, guinea pigs, etc. as well as animals in captivity such as animals of zoos. The term "animal" as used herein also includes humans.

The pharmaceutical compositions of the invention are preferably sterile and contain an effective amount of the particles of the invention and optionally of further agents as discussed herein such as therapeutic agents and antigens to generate the desired reaction or the desired effect.

The pharmaceutical composition of the invention may be formulated as an emulsion containing an oil such as Montanide®.

The pharmaceutical composition of the invention may also comprise an additional immunomodulating agent such as anti-CTL-A4 or anti-regulatory T-cell reagents such as an anti-CD25 antibody or cyclophosphamide.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CFS, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Because of the presence of the immunostimulating agent according to the invention comprising ssRNA and dsRNA as the primary immunostimulants, however, only a relatively small amount of CpG DNA is necessary (compared with immunostimulation with only CpG DNA). Thus, CpG DNA could be added in the ssRNA/dsRNA mixture before addition of protamine so that all nucleic acids are condensed within particles or added on preformed protamine/ssRNA/dsRNA particles. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, INFα, INF-γ, GM-CSF, LT-α, or growth factors, e.g. hGH. Further known adjuvants are aluminium hydroxide, Freund's adjuvant or oil such as Montanide®, most preferred Montanide® ISA51.

Lipopeptides, such as Pam3Cys, are also suitable for use as adjuvants in the pharmaceutical composition of the present invention.

Pharmaceutical compositions are usually provided in a uniform dosage form and may be prepared in a manner known per se. The pharmaceutical composition of the invention may e.g. be in the form of a solution or suspension.

The pharmaceutical composition of the invention may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in the pharmaceutical composition of the invention include acetic acid in a salt, citric acid in a salt, boric acid in a salt and phosphoric acid in a salt.

Suitable preservatives for use in the pharmaceutical composition of the invention include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition of the present invention and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The following examples are intended to illustrate preferred embodiments of the invention and should not be interpreted to limit the scope of the invention as defined in the claims.

EXAMPLES

Example 1

Method for the Preparation of an Immunostimulatory Protamine/ssRNA/dsRNA Particle Composition An oligoribonucleotide of approximately 18 residues is synthesized and purified. The product is then lyophilized and resuspended at 1 mg/ml in pure water. Polyinosinic acid and polycytidylic acid are chemically synthesized, purified and hybridized before being lyophilized and resuspended at 1 mg/ml in pure water. Protamine Valeant® 5000 is diluted 14 times in pure water to provide a solution of protamine at approximately 1 mg/ml in low salt. The oligoribonucleotide and the hybridized polyinosinic-polycytidylic acid are mixed at equal amounts. Then, 4 volumes of 1 mg/ml protamine are added. Immediate and intensive mixing is performed for example by pipeting up and down or by vortexing. The formulation is left for a few minutes on the bench and can then be further diluted with injection solution (for example Ringer lactate) or mixed with the antigen and eventually Montanide®. Should the protamine/ssRNA/dsRNA particle solution be too diluted, the particles can be recovered by centrifugation or freeze drying and be resuspended in the adequate volume of desired solution before being used for treatment formulation.

Example 2

Raw Physical Data Obtained from Size and Composition Measurement Experiments for Protamine/ssRNA/dsRNA Compositions The 18 mer U rich ssRNA oligonucleotide (RNA18: 5' AGUGUUAUUCUUGUAUGG 3', (SEQ ID NO: 1); stock solution at 5 mg/ml in water, "R18"), high molecular weight (HMW, average length of the RNA molecules is from 1500 to 8000 base pairs) and Low Molecular Weight (LMW, average length of the RNA molecules is from 200 to 1000 base pairs) dsRNA (Poly(I:C) composed of a strand of poly(I) annealed to a strand of poly(C)) and Protamine VALEANT® 5000 (14 mg/ml stock solution in an isotonic injection solution, "P") were diluted to 1 mg/ml using water, 25 mM NaCl, 75 mM NaCl or 125 mM NaCl. A total of 5 micrograms of RNA (either 5 micrograms of one species of RNA or a mixture of 2.5 micrograms of ssRNA and 2.5 micrograms of dsRNA) was mixed with 10 micrograms of protamine (protamine-RNA ratio: 2-1).

Three minutes after adding protamine to the RNA, 1 ml of Ringer lactate was added and the whole solution transferred to a transparent cuvette. The cuvette was placed in a Malvern Zetasizer and the size of the particles was measured as well as the Polydispersity. In general, good polydispersity (i.e. homogeneity of the particles) is bellow 0.1. The software also gives a "pass" or "fail" quality factor which relates to the quality of the measurement. A "fail" criteria means that the particle size distribution is heterogenous or that there are aggregates for example. Each experiment was repeated several times and the median values are reported in the below table. When some conditions led alternatively to a "pass" or "fail" quality factor, "Pass/Fail" is given.

|  | Water | 25 mM NaCl | 75 mM NaCl | 125 mM NaCl |
|---|---|---|---|---|
| Median size | | | | |
| P-R18 | 334.3 | 281.3 | 554.7 | 1112.7 |
| P-HMW | 342.3 | 318 | 413 | 597 |
| P-LMW | 14147.5 | 2530.1 | 1298.7 | 4407 |
| P-R18-HMW | 328.8 | 343 | 403.3 | 370 |
| P-R18-LMW | 305.8 | 307.3 | 669.9 | 13908.3 |
| Median Polydispersity | | | | |
| P-R18 | 0.06 | 0.06 | 0.18 | 0.26 |

-continued

|  | Water | 25 mM NaCl | 75 mM NaCl | 125 mM NaCl |
|---|---|---|---|---|
| P-HMW | 0.75 | 0.77 | 1 | 1 |
| P-LMW | 1 | 1 | 0.76 | 1 |
| P-R18-HMW | 0.15 | 0.18 | 0.4 | 1 |
| P-R18-LMW | 0.05 | 0.09 | 0.45 | 1 |
| Quality factor | | | | |
| P-R18 | Pass | Pass | Pass | Pass |
| P-HMW | Fail | Fail | Fail | Fail |
| P-LMW | Fail | Fail | Fail | Fail |
| P-R18-HMW | Pass | Pass | Pass/Fail | Pass/Fail |
| P-R18-LMW | Pass | Pass | Pass | Fail |

As found earlier, when ssRNA (RNA18) and protamine are diluted in low salt solutions (less than 125 mM NaCl), homogenous nanoparticles are obtained. Homogeneity (polydispersity) is best when the salt concentration in the diluting solution is 25 mM NaCl or bellow. It is demonstrated here that dsRNA (both HMW and LMW) when mixed with protamine fails to give particles of good quality even when reagents are diluted with low salt solutions (high polydispersity and "fail" quality factor). However, unexpectedly and surprisingly, when dsRNA is mixed with ssRNA (RNA18), the addition of protamine allows to generate nanoparticles of good quality in particular when reagents are diluted in pure water or 25 mM NaCl. When mixed with RNA18, LMW dsRNA tends to provide more homogenous (polydispersity bellow 0.1) particles than HMW dsRNA mixed with RNA18.

Figure 1:
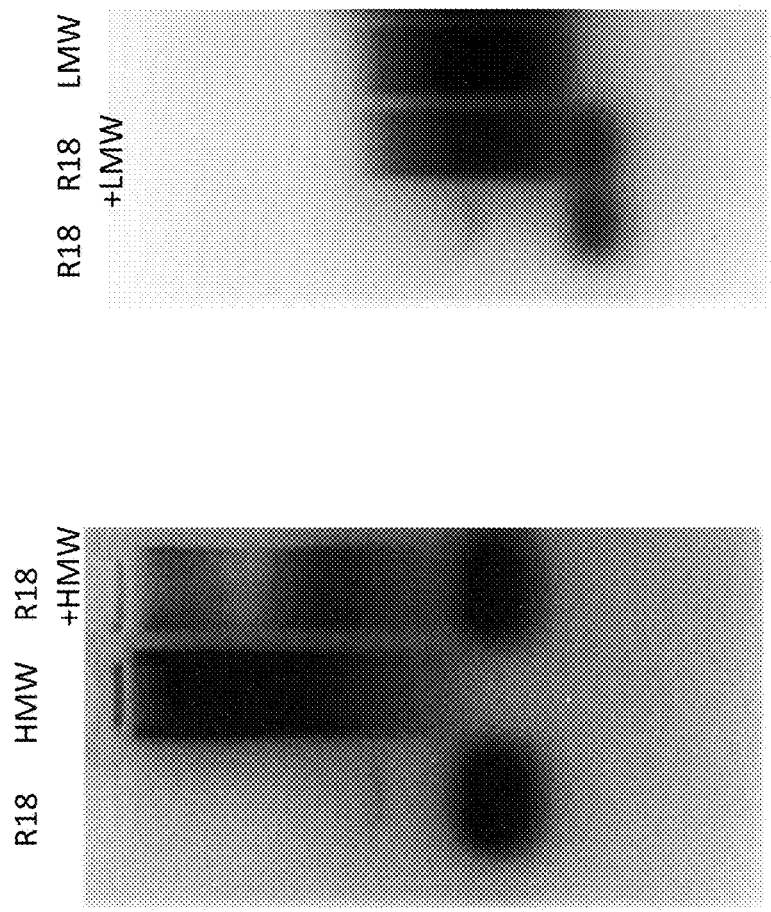
FIG. 1: Addition of protamine to premixed ssRNA and dsRNA allows to generate chimeric protamine/ssRNA/dsRNA particles containing both the dsRNA and the ssRNA.

RNA and protamine were diluted to 1 mg/ml using pure water. 5 micrograms of RNA (ssRNA:RNA18 or dsRNA or a mixture of 2.5 micrograms of ssRNA with 2.5 micrograms of dsRNA) were mixed with 10 micrograms of protamine. Three minutes later the solutions were centrifuged 3 min at 10,000 rpm in a table top centrifuge. The supernatants were then removed carefully with a yellow tip attached to a micropipette. The particles (pellets) were resuspended in 10 microliters of water containing 0.5% sodium dodecyl sulfate (SDS) and 2 microliters of 10 mg/ml proteinase K were added. All mixtures were incubated at 37° C. for 30 minutes so that protamine is digested and RNA molecules released free. Then, 3 microliters of loading buffer containing 0.5% SDS were added to all samples. The formulations were loaded on a 2% native agarose gel and migrated at 2V/cm during one to two hours. The gel on the left of FIG. 1 shows an example of the results obtained with HMW dsRNA and the gel on the right shows an example of the results obtained with LMW dsRNA. "R18" is ssRNA alone, "HMW" is high molecular weight dsRNA, "LMW" is low molecular weight dsRNA, "R18+HMW" is a mixture of RNA18 and HMW dsRNA, "R18+LMW" is a mixture of RNA18 and LMW dsRNA. It is demonstrated that both ssRNA and dsRNA alone or mixed together get trapped in the particles (found in the pellets); see FIG. 1. Thus, when ssRNA and dsRNA are premixed, the addition of protamine allows to generate chimeric protamine/ssRNA/dsRNA particles containing both the dsRNA and the ssRNA.

Example 3

Immunostimulation Capacity of Protamine/ssRNA/dsRNA Particles as Reflected by Interferon-Alpha Production PBMCs from a healthy human donor were prepared using Ficoll® gradient separation. They were then washed with PBS and resuspended at 5 million per ml in RPM' with 10% fetal calf serum plus penicillin and streptomycin. Two hundred microliters (1 million of cells) were added in wells from a 96 well plate on top of 4 micrograms of protamine ("Prot")
2 micrograms of ssRNA, oligonucleotide RNA18 ("R18")
2 micrograms of High Molecular Weight dsRNA ("HMW")
4 micrograms of protamine mixed with 2 micrograms of ssRNA ("Prot-R18")
4 micrograms of protamine mixed with 2 micrograms of High Molecular Weight dsRNA ("Prot-HMW")
4 micrograms of protamine mixed with 1 microgram of ssRNA and 1 microgram of High Molecular Weight dsRNA ("Prot-R18-HMW")
2 micrograms of Low Molecular Weight dsRNA ("LMW")
4 micrograms of protamine mixed with 2 micrograms of Low Molecular Weight dsRNA ("Prot-LMW")
4 micrograms of protamine mixed with 1 microgram of ssRNA and 1 microgram of Low Molecular Weight dsRNA ("Prot-R18-LMW")

As negative control, PBMCs were cultured alone.

These preparations were incubated for 18-24 hours at 37° C. with 5% CO2. Then, the supernatants of the cultures were collected. The content of IFN-alpha in these supernatants was evaluated using 20 microliters of supernatants and ELISA kits from Bender. The results are presented in FIG. 2 in pg/ml in the cell culture supernatant. They demonstrate that chimeric particles containing ssRNA and dsRNA (high or low molecular weight) are immunostimulating. In general, interferon-alpha production was superior using stimulation with chimeric particles (ssRNA+dsRNA) than when using particles contained only ssRNA. The addition of protamine on dsRNA was not increasing (and rather decreasing the minimal interferon-alpha induction observed in some experiments by naked dsRNA) its immunostimulating activity as judged by interferon-alpha production. Thus it is surprising that chimeric particles containing both ssRNA and dsRNA are capable to induce high interferon-alpha production.

Example 4

Immunostimulation Capacity of Protamine/ssRNA/dsRNA Particles as Reflected by Interferon-Beta Production PBMCs from a healthy human were prepared using Ficoll® gradient separation. They were then washed with PBS and resuspended at 5 million per ml in RPMI with 10% fetal calf serum plus penicillin and streptomycin. Two hundred microliters (1 million of cells) were added in wells from a 96 well plate on top of:

4 micrograms of protamine ("Prot")
2 micrograms of ssRNA, oligonucleotide RNA18 ("R18")
2 micrograms of High Molecular Weight dsRNA ("HMW")
4 micrograms of protamine mixed with 2 micrograms of ssRNA ("Prot-R18")
4 micrograms of protamine mixed with 2 micrograms of High Molecular Weight dsRNA ("Prot-HMW")
4 micrograms of protamine mixed with 1 microgram of ssRNA and 1 microgram of High Molecular Weight dsRNA ("Prot-R18-HMW")
2 micrograms of Low Molecular Weight dsRNA ("LMW")
4 micrograms of protamine mixed with 2 micrograms of Low Molecular Weight dsRNA ("Prot-LMW")

4 micrograms of protamine mixed with 1 microgram of ssRNA and 1 microgram of Low Molecular Weight dsRNA ("Prot-R18-LMW")

As negative control, PBMCs were cultured alone.

These preparations were incubated for 18-24 hours at 37° C. with 5% CO2. Then, the supernatants of the culture were collected. The content of intetrferon-beta in these supernatants was evaluated using 100 microliters of supernatants and ELISA kits from eBioscience. The results are presented in FIG. 3 in International Units (IU)/ml in the cell culture supernatant. They demonstrate that chimeric particles containing ssRNA and dsRNA (high or low molecular weight) are immunostimulating. In general, interferon-beta production was superior using stimulation with chimeric particles (ssRNA+dsRNA) than when using particles containing only ssRNA. The addition of protamine on dsRNA was not increasing but rather decreasing its immunostimulating activity as judged by interferon-beta production. Thus it is surprising that chimeric particles containing both ssRNA and dsRNA are capable to induce high interferon-beta production.

Example 5

Immunostimulation Capacity of Protamine/ssRNA/dsRNA Particles as Reflected by Interferon-Alpha Production Using Different Protamine/Total RNA Ratios PBMCs from a healthy human were prepared using Ficoll® gradient separation. They were then washed with PBS and resuspended at 5 million per ml in RPMI with 10% fetal calf serum plus penicillin and streptomycin. Two hundred microliters (1 million of cells) were added in wells from a 96 well plate on top of:
1 microgram of ssRNA (RNA18) and 1 microgram of High Molecular Weight dsRNA ("0 for 1")
2 micrograms of protamine mixed with 1 microgram of ssRNA (RNA18) and 1 microgram of High Molecular Weight dsRNA ("1 for 1")
4 micrograms of protamine mixed with 1 microgram of ssRNA (RNA18) and 1 microgram of High Molecular Weight dsRNA ("2 for 1")
8 micrograms of protamine mixed with 1 microgram of ssRNA (RNA18) and 1 microgram of High Molecular Weight dsRNA ("4 for 1")

These preparations were incubated for 18-24 hours at 37° C. with 5% CO2. Then, the supernatants of the culture were collected. The content of interferon-alpha in these supernatants was evaluated using respectively 20 microliters of supernatants and the ELISA kit from Bender. The results are presented in FIG. 4 in pg/ml in the cell culture supernatant. They demonstrate that as shown earlier, addition of protamine on a mixture of ssRNA and dsRNA allows stimulation of immune cells at protamine-RNA mass ratios from 1-1 up to 4-1.

Example 6

Synergistic Immunostimulating Activity of ssRNA and dsRNA as Far as Interferon-Alpha Production by Plasmacytoid DC is Concerned Depends on Third Cell Type(s)

PBMCs from a healthy human were prepared using Ficoll® gradient separation. They were then washed with PBS and resuspended at 20 million per ml in RPMI with 10% fetal calf serum plus penicillin and streptomycin. Half a ml of cells was incubated with pDC specific magnetic beads (positive sorting using BDCA-4 beads from Myltenyi) and run on magnetic column. After washing, the BDCA-4-positive enriched fraction was recovered. In this cell population, pDCs (BDCA-2 positive) represent more than 50% (in initial whole PBMCs, pDCs represent less than 1% of the cells). Recovered cells were diluted in 1.2 ml of complete medium and two hundred microliters of this cell suspension were added to the particles formed in the well of a 96 well plate by mixing:
  2 micrograms of ssRNA (RNA18) with 8 micrograms of protamine (both reagents at 1 mg/ml diluted in pure water). ("Prot-R18")
  2 micrograms of dsRNA (high molecular weight poly (I:C)) with 8 micrograms of protamine (both reagents at 1 mg/ml diluted in pure water). ("Prot-HMW")
  1 microgram of ssRNA (RNA18) and 1 microgram of dsRNA (poly(I:C)) with 8 micrograms of protamine (all reagents at 1 mg/ml diluted in pure water) ("Prot-R18-HMW")

The negative control is the same pDC-enriched cell population cultured in the presence of 8 micrograms of protamine ("Prot").

These preparations were incubated for 18-24 hours at 37° C. with 5% CO2. Then, the supernatants of the culture were collected. The content of IFN-alpha in these supernatants was evaluated using 20 microliters of supernatants and ELISA kits from Bender. The results are presented in FIG. 5 in pg/ml in the cell culture supernatant. They demonstrate that the high interferon-alpha production in PBMCs induced by chimeric particles containing 1 microgram of ssRNA and 1 microgram of dsRNA is not obtained in enriched pDCs cell suspension. Protamine-based particles containing 2 micrograms of ssRNA are superior in stimulating sorted pDCs compared to chimeric particles containing 1 microgram of ssRNA and 1 microgram of dsRNA. Thus, the capacity of the protamine/ssRNA/dsRNA particles to induce high interferon-alpha production in PBMC depends probably on the stimulation by those chimeric particles of other cells in addition to pDCs. Those cells may produce interferon-alpha or they may produce mediators that further activate pDCs, enhancing their interferon-alpha production.

Example 7

Immunostimulating Capacity of Protamine/ssRNA/dsRNA Particles Versus Protamine/ssRNA Mixed with Protamine/dsRNA as Reflected by Interferon-Alpha Production PBMCs from a healthy human donor were prepared using Ficoll® gradient separation. They were then washed with PBS and resuspended at 5 million per ml in RPMI with 10% fetal calf serum plus penicillin and streptomycin. Two hundred microliters (1 million of cells) were added in wells from a 96 well plate on top of
2 or 4 micrograms of protamine ("2micProt" and "4micProt", respectively)
2 micrograms of ssRNA, oligonucleotide RNA18 ("2micR18")
2 micrograms of Low Molecular Weight dsRNA ("2micLMW")
1 microgram of ssRNA, oligonucleotide RNA18 mixed with 1 microgram of Low Molecular Weight dsRNA ("1micR18+1micLMW")

4 micrograms of protamine mixed with 2 micrograms of ssRNA ("4micProt+2micR18")

4 micrograms of protamine mixed with 2 micrograms of Low Molecular Weight dsRNA ("4micProt+2micLMW")

4 micrograms of protamine mixed with 1 microgram of R18 combined with 1 microgram of Low Molecular Weight dsRNA ("4micProt+1micR18+1micLMW")

A mixture of two independent formulations ("2micProt+1micR18+2micProt+1micLMW"): the first one containing 2 microliters of protamine mixed with 1 microgram of single stranded RNA and the second one containing 2 microliters of protamine mixed with 1 microgram of dsRNA.

As negative control, PBMCs were cultured alone.

These preparations were incubated for 18 hours at 37° C. with 5% CO2. Then, the supernatants of the cultures were collected. The content of IFN-alpha in these supernatants was evaluated using 20 microliters of supernatants and ELISA kits from Bender. The results are presented in FIG. 6 in pg/ml in the cell culture supernatant. They demonstrate that chimeric particles containing both ssRNA and dsRNA are more immunostimulating than a mixture of two formulations containing protamine+ssRNA and protamine+dsRNA. Thus chimeric protamine-based particles containing both ssRNA and dsRNA are capable to induce higher interferon-alpha production than a combination of independent protamine-ssRNA and protamine-dsRNA formulations.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. Furthermore, the teachings and disclosures of all references cited herein are expressly incorporated in their entireties by reference.

The invention claimed is:

1. A homogeneous chimeric particle comprising a complex;
    wherein the complex consists of at least one cationic agent, a single stranded RNA (ssRNA) and a double stranded RNA (dsRNA); wherein the at least one cationic agent comprises protamine; wherein the complex is formed by the addition of the at least one cationic agent to premixed ssRNA and dsRNA; and wherein the dsRNA comprises two RNA molecules fully or partially hybridized together.

2. The particle of claim 1, wherein the particle has a diameter in the range of from about 50 nm to about 1000 nm.

3. The particle of claim 1 or 2, wherein the at least one cationic agent encloses said RNA.

4. The particle of claim 1, wherein the at least one cationic agent comprises a polycationic compound.

5. The particle of claim 1, wherein the at least one cationic agent comprises at least one agent selected from the group consisting of an RNA-complexing lipid, an RNA complexing polymer, and an RNA-complexing peptide or protein.

6. The particle of claim 1, wherein the at least one cationic agent comprises at least one agent selected from the group consisting of polyethyleneimine, a poly-L-lysine, a poly-L-arginine or a histone.

7. The particle of claim 1, wherein the at least one cationic agent consists of protamine.

8. The particle of claim 1, wherein the protamine: RNA (ssRNA+dsRNA) weight ratio is from 16:1 to 1:2, preferably from 4:1 to 1:2.

9. The particle of claim 1, wherein the ssRNA contains at least one U nucleotide and/or at least one G nucleotide.

10. The particle of claim 1, wherein the ssRNA is an oligonucleotide of from 6 to 100 nucleotides or an mRNA of from 50 to 10,000 nucleotides.

11. The particle of claim 1, wherein the ssRNA is an oligonucleotide having the sequence according to SEQ ID NO: 1.

12. The particle of claim 1, wherein the strands of the dsRNA are in average from 6 to 8000 nucleotides in length.

13. The particle of claim 1, wherein the dsRNA is polyinosinic-polycytidylic acid (poly(I:C)).

14. The particle of claim 1 for use as an immunostimulant.

15. A pharmaceutical composition comprising the particle of claim 1 and optionally one or more pharmaceutically acceptable carriers, diluents and/or excipients.

16. The pharmaceutical composition of claim 15 which further comprises at least one adjuvant.

17. A method for stimulating the immune system of a subject comprising administering to the subject the pharmaceutical composition of claim 15 or 16.

18. The method of claim 17, wherein the pharmaceutical composition is co-administered with at least one antigen.

19. A method for the preparation of homogeneous chimeric particles comprising the steps of:
    (a) providing an aqueous solution of single stranded RNA (ssRNA);
    (b) providing an aqueous solution of double stranded RNA (dsRNA);
    (c) providing an aqueous solution of protamine; and
    (d) combining the solutions obtained in steps (a) and (b) and mixing it with the solution obtained in (c); and
    wherein the chimeric particles comprise a complex consisting of protamine, ssRNA and dsRNA.

20. A method for the preparation of homogeneous chimeric particles comprising the steps of:

(a) providing an aqueous solution of single stranded RNA (ssRNA) at less than 5 mg/ml using a solution containing 0 to 125 mM electrolytes;
(b) providing an aqueous solution of double stranded RNA (dsRNA) at less than 5 mg/ml using a solution containing 0 to 125 mM electrolytes;
(c) providing an aqueous solution of protamine at less than 5 mg/ml using a solution containing 0 to 125 mM electrolytes; and
(d) combining the solutions obtained in steps (a) and (b) and adding the solution obtained in (c); and
wherein the chimeric particles comprise a complex consisting of protamine, ssRNA and dsRNA.

21. The method of claim 19 or 20, wherein step (a) and/or step (b) comprises resuspending dried RNA in an aqueous solution containing 0 to 125 mM electrolytes.

22. The method of claim 19 or 20, wherein step (c) comprises diluting an aqueous isotonic stock solution containing 1000 to 5000 heparin-neutralizing units of protamine per ml with an aqueous solution containing 0 to 125 mM electrolytes.

23. The method of claim 19 or 20 comprising the steps of:
(a) providing an aqueous solution of ssRNA at less than 5 mg/ml by resuspending dried ssRNA in pure water;
(b) providing an aqueous solution of dsRNA at less than 5 mg/ml by resuspending dried dsRNA in pure water;
(c) providing an aqueous solution of protamine at less than 5 mg/ml by diluting an aqueous isotonic stock solution containing 5000 heparin-neutralizing units of protamine per ml with pure water; and
(d) combining the solutions obtained in steps (a) and (b) and adding the solution obtained in (c).

* * * * *